United States Patent
Holmes et al.

Patent Number: 5,176,648
Date of Patent: Jan. 5, 1993

[54] INTRODUCER ASSEMBLY AND INSTRUMENT FOR USE THEREWITH

[75] Inventors: Jeffrey E. Holmes; Jeffrey J. Christian, both of San Jose, Calif.

[73] Assignee: Unisurge, Inc., Cupertino, Calif.

[21] Appl. No.: 807,101

[22] Filed: Dec. 13, 1991

[51] Int. Cl.⁵ .................... A61M 5/178; A61M 5/32
[52] U.S. Cl. .................... 604/164; 604/180
[58] Field of Search ........... 604/164, 158, 167, 169, 604/264, 174, 268, 180

[56] References Cited

U.S. PATENT DOCUMENTS

| | | | |
|---|---|---|---|
| 4,419,094 | 12/1983 | Patel | 604/158 |
| 4,755,173 | 7/1988 | Konopka et al. | 604/180 |
| 4,817,631 | 4/1989 | Schnepp-Pesch et al. | 604/167 |
| 4,904,240 | 2/1990 | Hoover | 604/167 |
| 4,909,798 | 3/1990 | Fleischhacker et al. | 604/167 |
| 5,059,186 | 10/1991 | Yamamoto et al. | 604/167 |
| 5,073,169 | 12/1991 | Raiken | 604/180 |

*Primary Examiner*—Gene Mancene
*Assistant Examiner*—Todd E. Manahan
*Attorney, Agent, or Firm*—Flehr, Hohbach, Test, Albritton & Herbert

[57] ABSTRACT

In an introducer assembly for introduction into a cavity of a patient having skin overlying the cavity and permitting the introduction of an instrument therethrough, and elongate tubular member having a flow passage extending therethrough and having proximal and distal extremities, a flange having top and bottom sides and having an inner margin with an opening therein through which the tubular member extends with the proximal extremity of the tubular member being disposed on the bottom side of the flange, releasable retaining means engaging the inner margin of the flange and the tubular member for forming a fluid-tight seal between the inner margin of the flange and the tubular member and permitting adjustment of the tubular member longitudinally in said opening, said valve means carried by the proximal extremity of the tubular member for inhibiting the flow of fluid through said flow passage from the distal extremity to the proximal extremity and permitting instruments to be inserted through the same while maintaining substantially fluid-tight seal and adhesive means secured to the bottom side of said flange for engaging the skin of the patient for retaining the flange in sealing engagement with the skin of the patient.

9 Claims, 1 Drawing Sheet

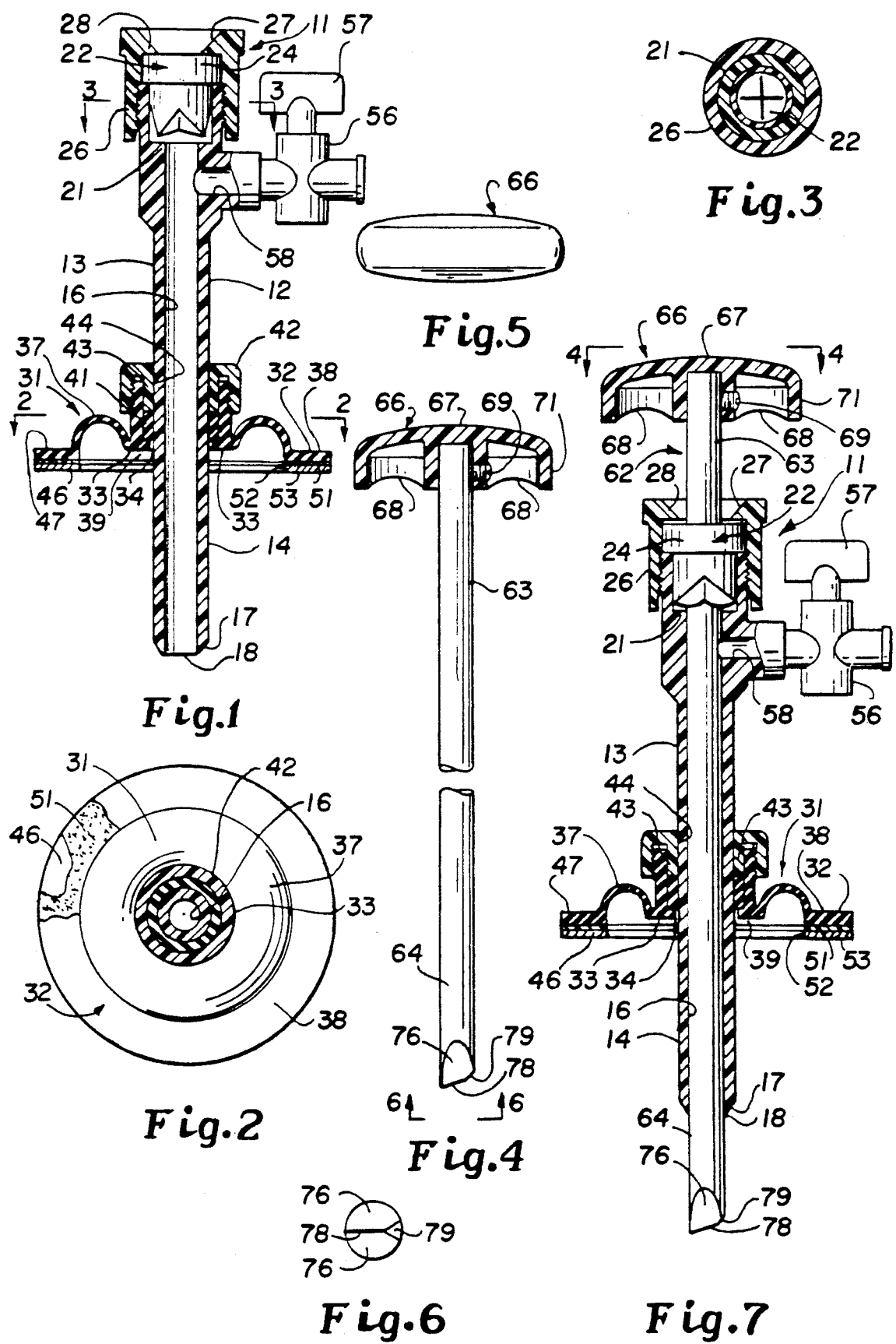

INTRODUCER ASSEMBLY AND INSTRUMENT FOR USE THEREWITH

This invention relates to an introducer assembly and instrument for use therewith, often called a trocar.

Trocars, heretofore, have been provided for use in medical procedures. However, the introducer device utilized in such trocars introduced through the abdominal wall of a patient tends to come out during the medical procedure during movement of the introducer, as for example when the physician is manipulating tools in the introducer and also because of the positive pressure of gas in the abdomen of the patient. Attempts have been made to solve this problem by forming devices on the introducer to inhibit the introducer tube from being displaced from the abdominal wall of the patient. However, such devices have been unduly complicated and not particularly efficacious in solving the problem. In addition, the cutting tool or instrument utilized in such trocars typically has been provided with three facets which create a wound in the skin which when healed forms undesirable scar tissue. There is, therefore, a need and an instrument for making a wound which will heal more readily without undesirable scar tissue.

In general, it is an object of the present invention to provide an introducer assembly and an instrument for use therewith which can be easily used.

Another object of the invention is to provide an introducer assembly of the above character having a large flange with a tubular member extending therethrough and in which the flange is secured to the exterior surface of the skin of a patient as, for example, on the abdominal wall of the patient.

Another object of the invention is to provide an introducer assembly of the above character in which the length of the tubular member below the flange and entering into the patient can be readily adjusted.

Another object of the invention is to provide an introducer assembly of the above character in which the flange permits sidewise or pivotal movement of the proximal extremity of the tubular member without affecting the seal formed with the skin of the patient.

Another object of the invention is to provide an introducer assembly of the above character which is provided with the sealing means within the tubular member which readily permits the introduction of instruments therethrough while maintaining a hemostatic seal.

Another object of the invention is to provide an introducer assembly of the above character having a flexible tubular member permitting the introduction of curved instruments therethrough.

Additional objects and features of the invention will appear from the following description in which the preferred embodiments are set forth in detail in conjunction with the accompanying drawings.

FIG. 1 is a side elevational view of an introducer assembly incorporating the present invention.

FIG. 2 is a cross-sectional view taken along the line 2—2 in FIG. 1.

FIG. 3 is a cross-sectional view taken along the line 3—3 in FIG. 1.

FIG. 4 is a side elevational view of a cutting instrument for use with the introducer assembly shown in FIG. 1.

FIG. 5 is a top plan view looking along the line 5—5 of FIG. 4.

FIG. 6 is a bottom plan view looking along the line 6—6 of FIG. 4.

FIG. 7 is a side elevational view of the introducer assembly shown in FIG. 1 with the instrument shown in FIG. 4 disposed therein.

In general, the introducer assembly is used for introduction into a cavity of a patient having skin overlying the cavity and permitting the introduction of an instrument therethrough. The introducer assembly consists of an elongate tubular member having a passage extending therethrough and having proximal and distal extremities.

A flange is provided having top and bottom sides and having an inner margin with an opening therein. The tubular member extends through the opening with the proximal extremity of the tubular member being disposed on the top side and the distal extremity being disposed on the bottom side of the gauge. Means is provided engaging the inner margin of the flange and the tubular member for forming a fluid-tight hemostatic seal between the inner margin of the flange and the tubular member and permitting adjustment of the tubular member longitudinally in said opening. Valve means is carried by the proximal extremity of the tubular member for inhibiting flow of fluid through the passage in the tubular member from the distal extremity to the proximal extremity. The valve means is formed to permit the instrument to be inserted in to the passage and for withdrawing the instrument from the passage while maintaining a substantially fluid-tight seal during use of the instrument.

More specifically, as shown in FIGS. 1–3, the introducer assembly 11 consists of a tubular member 12 formed of a suitable material such as a medical grade plastic that has a wall thickness such that the tubular member 12 is relatively rigid. If a flexible tubular member 12 is desired a plastic thin wall tube having high resilience and low rigidity is utilized formed of a urethane or polyethylene-type material. The tubular member 12 is provided with a proximal extremity 13 and a distal extremity 14 and has a flow passage 16 extending therethrough. The distal extremity 14 is provided with a taper 17 extending inwardly and downwardly to a relatively sharp circular edge 18. The proximal extremity 13 of the tubular member 12 is provided with an enlarged portion 21 which received a flexible valve member 22 of the type described in copending application Ser. No. 07/757,343, filed Sept. 10, 1991.

As disclosed in that application, the valve member 22 is comprised of three V-shaped leaflets 23 which form a hemostatic seal to prevent, or at least inhibit, the flow of fluids, that is, gases or liquids, through the flow passage 16 from the distal extremity 14 to the proximal extremity 13. The valve member 22 is also formed to permit the introduction of instruments therethrough and into the flow passage 16 as hereinafter described while still retaining a fluid-tight hemostatic seal with respect to that instrument. The valve member 22 is provided with a flange 24 which sits upon the upper extremity of the enlarged portion 21 and is retained in engagement therewith by a cap 26 which is threaded onto the upper extremity of the enlarged portion 21 (see FIG. 1). A cap 26 is provided with a conical opening 27 therein which is in registration with the center of the valve member 22. The cap 26 is provided with an inwardly and radially extending flange 28 which overlies and engages the flange 24 of the valve member to retain it in place.

The introducer assembly 11 is also provided with retaining means for retaining the tubular member 12 in a cavity of the patient after it has been introduced into the cavity of the patient. This retaining means consists of a flange assembly 31 which is releasably secured to the tubular member 12 so that the length of the tubular member which extends through the flange can be adjusted. The flange assembly 31 consists of a large molded flange 32 three to four inches in diameter formed of a relatively flexible rubbery material. One material found particularly suitable is Krayton (trademark) of medium durometer which is manufactured by Shell Corporation of Houston, Tex. The flange 32 as shown in FIG. 2 is circular in form. However, it should be appreciated that other shapes such as rectangle can be utilized if desired.

The flange 32 is provided with an inner margin 33 and circumscribed by the inner margin 33 to an opening 34. The tubular member 12 extends through the opening 34 which also circumscribes the opening 34. The flange 32 is provided with a thin annular rib or convolution 37 which is semi-circular in cross-section with a reduced cross-sectional thickness in comparison to the other portions of the flange to permit flexure-type movements of the collar 36 with respect to the outer margin 38 of the flange 32. The inner margin 33 is positioned above the outer margin 38 so that there is provided a space 39 underlying the inner margin 33. Thus, the rib or convolution 37 serves as a bellows-like or an accordion-like device to permit tilting or pivotal movement of the collar 36 with respect to the outer margin 38 of the flange 32.

A circular cylindrical flexible gasket 41 formed of a suitable material such as silicone is disposed between the collar 36 and the outer surface of the tubular member 12. Means is provided for compressing this gasket 41 so that it forms a fluid-tight seal between the inner margin 33 of the flange 32 and the tubular member and consists of a cap 42 formed of suitable material such as plastic which is threaded onto the outer surface of the collar 36. The cap 42 formed of suitable material such as plastic which is threaded onto the outer surface of the collar 36. The cap 42 is provided with a downwardly-extending cylindrical flange 43 which circumscribes an opening 44 provided in the cap. As can be seen, as the cap 42 is tightened, the downwardly-extending flange 42 engages the gasket 41 to compress the material of the gasket to force the same into a fluid-tight sealing engagement with the tubular member 12 and the collar 13. By unthreading the cap 42, the pressure created by the gasket on the tubular member 12 can be relieved, permitting the tubular member 12 to be adjusted longitudinally of the flange assembly 31 to provide different lengths of the tubular member 12 extending distally or below the bottom surface 46 of the flange 32. Thus, the tubular member 12 is disposed below the bottom side or surface 46 of the flange 32 and the proximal extremity 13 is disposed above the top side or surface 47 of the flange 32.

Means is provided for securing the bottom surface 46 of the flange 32 to the skin of a patient, as for example, to the skin on the abdominal wall of the patient. This means can take the form of a disk 51 which is provided with adhesive on each side. One material found to be particularly suitable for this application is an adhesive No. 1500 sold by 3M Company of St. Paul, Minneapolis/Minn. 55101 under the trademark "Stomaseal". The disk 51 is provided with a central opening 52 so that the disk 51 only covers the outer margin of the flange 32 beyond the rib 37. A paper protective covering 53 is provided on the outer exterior surface of the disk 51 which can be readily removed when it is desired to utilize the introducer assembly 11 as hereinafter described.

A stop cock 56 with an operating handle 57 is mounted on the tubular member 12 just below the valve member 22. The stop cock 56 is provided with a flow passage 58 in communication with the flow passage 16 in the tubular member 12.

The cutting instrument 6 for use with the introducer assembly 11 is shown in FIGS. 4-6. As shown therein, the cutting instrument 61 consists of a cylindrical shaft 62 formed of a suitable medical grade metal as, for example, Series 304 stainless steel. The shaft is provided with proximal and distal extremities 63 and 64. A handle 66 is mounted on the proximal extremity 63. The handle 66, as shown, is elongate in form and is provided with a curved upper surface which is adapted to be engaged by the palm of the human hand. It is also provided with arcuate recesses 68 on the under surface of the same which are adapted to be engaged by the fingers of the hand engaging the handle. The handle 66 can be formed of a suitable material such as plastic and is secured to the proximal extremity 63 in a suitable manner such as by a set screw 69 accessible through an opening 71 provided in the handle.

Cutting means is provided on the distal extremity 64 of the cutting instrument 61 and is usually formed by downwardly and inwardly inclined surfaces 76 and 77 formed on the distal extremity which intersect to form a chisel-like straight cutting edge 78 which is inclined upwardly in from a horizontal plane perpendicular to the longitudinal axis of the shaft 62. The tapered or inclined surfaces 76 and 77 and 79 can be formed in a suitable manner such as by grinding. The left-hand side of the cutting edge 78 as viewed in FIG. 3 forms a sharp scalpel-like cutting blade at one point to provide a concentrated force to penetrate the skin and then create a slicing action as the entire straight cutting edge penetrates the skin. The edges of the skin are separated by the tapered surfaces 76 and 77 as the cutting instrument 61 enters the cavity underlying the skin. The edges of the skin are then stretches as the circumference of the shaft 62 passes through the skin to form a good seal about the shaft 62. The other or right hand side of the cutting edge is relieved by providing a small taper 79 that inclines inwardly and downwardly with respect to the cutting edge 78 and extends at right angles to the cutting edge 78.

Operation and use of the introducer assembly 11 and the cutting instrument 61 in connection therewith may now be briefly described as follows. Let it be assumed that it is desired to perform certain medical procedures in the abdomen of a patient. In connection therewith, it is desired to place an introducer assembly 11 into the abdominal wall of the patient through which various instruments can be placed. The surface of the abdominal wall to be penetrated is scrubbed clean in a conventional manner after which the introducer assembly 11 with the cutting instrument 61 mounted therein can be taken by the physician and the protective covering 53 removed. Thereafter, the introducer assembly 11 can be grasped in one hand by the physician and with the other hand grasping the handle 56. The introducer assembly 11 is then aligned so that eh cutting instrument 61 extends in a direction perpendicular to the surface of the skin of the patient in which the penetration is to be made. The physician then pushes on the handle 66 to force the straight cutting edge 78 through the skin of the patient to make a straight cut wound in the abdominal wall of the patient. As soon as the abdominal wall has been penetrated, the introducer assembly 11 is forced through the wound which has been made by the instrument and advanced to the desired depth in the abdominal cavity of the patient. Various lengths of the tubular member 12 can be readily provided by loosening of the cap 42 and extending and retracting the tubular member 12 with respect to the flange 32 and then tightening the same to establish a liquid-tight seal.

The adhesive surface of the disk 51 is then brought into contact with the abdominal wall of the patient to firmly secure the flange 32 to the exterior surface of the abdominal wall of the patient to retain the tubular member 12 in a stable position with respect to the abdominal wall. After the flange 32 has been properly secured to the abdominal wall of the patient, the cutting instrument 61 can be removed. The valve member 22 serves to form a fluid-tight seal with respect to the cutting instrument so that gases and fluids in the abdominal cavity cannot escape through the flow passage 16 from the distal extremity to the proximal extremity. After the cutting instrument 61 has been removed, the valve member seals on itself to still inhibit the escape of fluid from the abdominal cavity.

Thereafter, as desired, the physician can introduce other medical-type instruments through the introducer assembly by extending the same through the valve member and the instrument introduced through the flow passage 16. Because of the flexibility of the annular rib 37 in the flange 32, and the provision of the annular space 39, it is possible to move the instruments being utilized therein sideways, or in other words, by rocking or pivotal motion with respect to the plane formed by the flange 32 without disturbing the seal formed between the flange 32 and the abdominal wall of the patient. Also because of the flexibility of the tubular member 12, curved instruments can be introduced through the introducer assembly 11 and thereafter used in a manner similar to other instruments.

After the desired medical procedures have been accomplished, the introducer assembly 11 can be removed from the abdominal wall of the patient and the wound sutured. The wound when healed forms a straight linear scar which is virtually undetectable in the skin of the patient. It also forms a scar tissue which is much smaller than one which is formed with a convention three-faceted trocar.

From the foregoing, it can be seen that there has been provided a new and novel introducer assembly which serves as an obturator and which in combination with the cutting instrument forms a trocar. The introducer assembly is affixed to the external surface of the abdominal wall of the patient by the use of a self-adhesive flange which is provided with an inner flexible portio permitting pivotal movement of the tubular member with respect to the flange without disturbing the adhesion of the flange to he abdominal wall of the patient. The length of the tubular member extending beyond the flange can be readily adjusted while still maintaining a fluid-tight seal.

What is claim is:

1. An introducer assembly for introduction into a cavity of a patient having skin overlying the cavity and permitting the introduction of an instrument therethrough, comprising an elongate tubular member having a flow passage extending therethrough and having proximal and distal extremities, a flange having top and bottom sides and having an inner margin with an opening therein through which the tubular member extends with the proximal extremity of the tubular member being disposed on the bottom side of the flange, releasable retaining means engaging the inner margin of the flange and the tubular member for forming a fluid-tight seal between the inner margin of the flange and the tubular member and permitting adjustment of the tubular member longitudinally in said opening, valve means carried by the proximal extremity of the tubular member for inhibiting the flow of fluid through said flow passage from the distal extremity to the proximal extremity and permitting instruments to be inserted through the same while maintaining a substantially fluid-tight seal and adhesive means secured to the bottom side of said flange for engaging the skin of the patient for retaining the flange in sealing engagement with the skin of the patient, said inner margin having an annular convolution formed therein of a thickness which is less than that of the remainder of the inner margin to permit pivotal movement of the tubular member in said flange without disturbing the sealing engagement of the flange with the skin of the patient.

2. An introducer assembly as in claim 1 wherein said flange is formed of Krayton.

3. An introducer assembly for introduction into a cavity of a patient having skin overlying the cavity and permitting the introduction of an instrument therethrough, comprising an elongate tubular member having a flow passage extending therethrough and having proximal and distal extremities, a flange having top and bottom sides and having an inner margin with an opening therein through which the tubular member extends with the proximal extremity of the tubular member being disposed on the bottom side of the flange, releasable retaining means engaging the inner margin of the flange and the tubular member for forming a fluid-tight seal between the inner margin of the flange and the tubular member and permitting adjustment of the tubular member longitudinally in said opening, valve means carried by the proximal extremity of the tubular member for inhibiting the flow of fluid through said flow passage from the distal extremity to the proximal extremity and permitting instruments to be inserted through the same while maintaining a substantially fluid-tight seal and adhesive means secured to the bottom side of said flange for engaging the skin of the patient for retaining the flange in sealing engagement with the skin of the patient, said releasable retaining means including a collar formed on the inner margin of said flange and encircling said tubular member, compressible gasket material disposed between the collar and the tubular member and the means secured to the collar engaging said gasket material to compress said gasket material to form said fluid-tight seal and permitting said tubular member to be adjusted in position longitudinally of said collar.

4. An introducer assembly for introduction into a cavity of a patient having skin overlying the cavity and permitting the introduction of an instrument therethrough, comprising an elongate tubular member having a flow passage extending therethrough and having proximal and distal extremities, a flange having top and bottom sides and having an inner margin with an opening therein through which the tubular member extends with the proximal extremity of the tubular member being disposed on the bottom side of the flange, releasable retaining means engaging the inner margin of the flange and the tubular member for forming a fluid-tight seal between the inner margin of the flange and the tubular member and permitting adjustment of the tubular member longitudinally in said opening, valve means carried by the proximal extremity of the tubular member for inhibiting the flow of fluid through said flow passage from the distal extremity to the proximal extremity and permitting instruments to be inserted through the same while maintaining a substantially fluid-tight seal and adhesive means secured to the bottom side of said flange for engaging the skin of the patient for retaining the flange in sealing engagement with the skin of the patient, a cutting instrument disposed within said flow passage and extending through said valve mean, said cutting instrument being provided with a solid shaft having a longitudinally extending axis and a straight cutting edge which is inclined upwardly from a horizontal plane perpendicular to the longitudinal axis of the shaft and which extends across substantially the width of the shaft.

5. An introducer assembly for introduction into a cavity of a patient having skin overlying the cavity and permitting the introduction of an instrument therethrough, comprising an elongated tubular member having a passage extending therethrough and having proximal and distal extremities, a flange having top and bottom sides and having an inner margin with an opening therein through which the tubular member extends with the proximal extremity of the tubular member being disposed on the top side of the flange and the distal extremity of the tubular member being disposed on the bottom side of the flange, said inner margin having annular convolution with a thickness less than that of the remainder of the inner margin to permit pivotal movement of the tubular member in the flange, means engaging the inner margin of the flange and the tubular member for forming a fluid-tight seal therebetween and valve means carried by the proximal extremity of the tubular member for inhibiting the flow of fluid through said passage from the distal extremity to the proximal extremity, said valve means being formed to permit said instrument to be inserted into the flow passage and withdrawn from the flow passage while maintaining a fluid-tight seal.

6. An assembly as in claim 5 together with adhesive means secured to the bottom side of said flange for securing said flange to the exterior surface of the skin of the patient and forming a sealing engagement therewith.

7. An assembly as in claim 6 wherein said means for forming a sealing engagement between the inner margin of said flange and said tubular member includes releasable means permitting said tubular member to be extended and retracted longitudinally through said opening in said flange.

8. A cutting instrument comprising a solid shaft having a longitudinal axis and having proximal and distal extremities, a handle adapted to be grasped by a human hand mounted on the proximal extremity of said shaft and cutting means formed on the distal extremity of the shaft, said cutting means being in the form of a straight cutting edge extending substantially across the width of the shaft and being inclined upwardly from a horizontal plane extending perpendicular to the longitudinal axis of the shaft.

9. A cutting instrument as in claim 8 wherein said shaft is cylindrical in cross-section and wherein said straight cutting edge extends diametrically of the shaft.

* * * * *